US010716821B2

(12) United States Patent
Legault et al.

(10) Patent No.: US 10,716,821 B2
(45) Date of Patent: Jul. 21, 2020

(54) USE OF PLANT EXTRACTS AGAINST HERPES SIMPLEX VIRUS

(71) Applicant: UNIVERSITÉ DU QUÉBEC À CHICOUTIMI, Chicoutimi (CA)

(72) Inventors: Jean Legault, La Baie (CA); André Pichette, Chicoutimi (CA); Isabelle Côté, Chicoutimi (CA); Serge Lavoie, Chicoutimi (CA)

(73) Assignee: UNIVERSITÉ DU QUÉBEC A CHICOUTIMI (CA)

( * ) Notice: Subject to any disclaimer, the term of this patent is extended or adjusted under 35 U.S.C. 154(b) by 701 days.

(21) Appl. No.: 14/906,783

(22) PCT Filed: Jul. 22, 2014

(86) PCT No.: PCT/CA2014/050693
§ 371 (c)(1),
(2) Date: Jan. 21, 2016

(87) PCT Pub. No.: WO2015/010205
PCT Pub. Date: Jan. 29, 2015

(65) Prior Publication Data
US 2016/0158300 A1  Jun. 9, 2016

Related U.S. Application Data (60) Provisional application No. 61/856,928, filed on Jul. 22, 2013.

(51) Int. Cl.
| | | |
|---|---|---|
| *A61K 36/68* | (2006.01) | |
| *A61K 36/40* | (2006.01) | |
| *A61K 36/00* | (2006.01) | |
| *A61K 36/28* | (2006.01) | |
| *A61K 36/48* | (2006.01) | |
| *A61P 31/22* | (2006.01) | |
| *A61K 36/896* | (2006.01) | |
| *A61K 36/88* | (2006.01) | |

(52) U.S. Cl.
CPC ............. *A61K 36/40* (2013.01); *A61K 36/28* (2013.01); *A61K 36/48* (2013.01); *A61K 36/68* (2013.01); *A61K 36/88* (2013.01); *A61K 36/896* (2013.01); *A61P 31/22* (2018.01); *A61K 2236/33* (2013.01); *A61K 2236/333* (2013.01)

(58) Field of Classification Search
None
See application file for complete search history.

(56) References Cited

U.S. PATENT DOCUMENTS

| | | | | |
|---|---|---|---|---|
| 4,646,725 A | * | 3/1987 | Moasser | ............ A61H 23/0245 601/2 |
| 5,434,183 A | | 7/1995 | Larsson-Backstrom | |
| 5,720,304 A | | 2/1998 | Omura | |
| 5,911,982 A | * | 6/1999 | Chao | .................... C07K 14/005 424/93.2 |
| 2001/0051184 A1 | | 12/2001 | Heng et al. | |
| 2006/0217438 A1 | | 9/2006 | Wilkins et al. | |
| 2010/0075914 A1 | | 3/2010 | Flacki et al. | |

FOREIGN PATENT DOCUMENTS

| | | |
|---|---|---|
| CA | 2106097 | 9/1992 |
| CA | 2206012 | 11/1998 |
| CA | 2334335 | 12/1999 |
| CA | 2428655 | 8/2002 |
| CA | 2527052 | 1/2005 |
| CA | 2533163 | 2/2005 |
| CA | 2573539 | 3/2006 |
| CA | 2629529 | 5/2006 |
| CA | 2663565 | 4/2008 |
| CN | 1077131 A | 10/1993 |
| CN | 1785407 A | 6/2006 |
| CN | 101049421 | 10/2007 |
| CN | 101049421 A * | 10/2007 |
| CN | 103041066 A | 4/2013 |
| EP | 00568001 A2 | 11/1993 |
| WO | 1998018491 A1 | 5/1998 |
| WO | 2002069992 A1 | 9/2002 |
| WO | 2015/010205 | 1/2015 |

OTHER PUBLICATIONS

Chinese Herbs healing—The Art of Herbal Remedies Revealed (printed Oct. 31, 2017)(www.ChineseHerbshealing.com/japanse-cornelian-cherry).
Côté, Isabelle, Evaluation De L 'Activite Antivirale De Cinq Especes Vegetales De La Foret Boreale Contre Les Virus Influenza De Type A Et L'Herpes Simplex De Type I, Masters Thesis, Universite Du Quebec A Chicoutimi, (confidentiality period ended Aug. 22, 2013).
Dharmananda s., Cornus (printed Nov. 1, 2017)(www.itmonline.org/arts/cornus.htm).
Isaak C.K. et al., Seasonal variations in phenolic compounds and antioxidant capacity of Cornus stolon if era plant material: Applications in agriculture, Can. J. Plant Sci. (2013) 93: 725-734.
EP14830173 Partial European Search Report dated Jan. 26, 2017.
EP14830173 Supplementary European Search Report and Opinion dated May 9, 2017.
Chayavichitsilp, et al., "Herpes simplex", Pediatrics in Review (2009), 30 (4):119-29.

(Continued)

*Primary Examiner* — Michael Barker
*Assistant Examiner* — Randall Winston
(74) *Attorney, Agent, or Firm* — Lavery, De Billy, LLP; Julie Gauvreau (57) ABSTRACT

The present invention provides a method of using a plant extract or active fraction thereof for inhibiting an herpes simplex virus (HSV) infection, wherein the plant is a: *Cornus* species; *Achillea* species; *Trifolium* species; *Trillium* species; and/or *Plantago* species. The present invention also provides plant extracts, active fractions, and compositions kits comprising same.

22 Claims, 3 Drawing Sheets

(56) References Cited

OTHER PUBLICATIONS

Coen, et al., "Thymidine kinase-negative herpes simplex virus mutants establish latency in mouse trigeminal ganglia but do not reactivate", Proc Natl Acad Sci USA, (1989), 86: 4736-4740.
Diaz, et al., "Novel targets for the development of anti-herpes compounds", Infectious Disorders Drug Targets, (2007), p. 11-18, vol. 7.
Jacobson, et al., "Importance of the herpes simplex virus UL24 gene for productive ganglionic infection in mice", Virology, (1998), 242: 161-169.
Jadhav, et al., "Antiviral Potential of Selected Indian Medicinal (Ayurvedic) Plants Against Herpes Simplex Virus 1 and 2", N Am J M Sci, (2012), p. 641-647, vol. 4, No. 12.
Koch, et al. "Inhibitory effect of essential oils against herpes simplex virus type 2", Phytomedicine, (2008), p. 71-78, vol. 15(1-2).
Leib, et al. "A Deletion Mutant of the Latency-Associated Transcript of Herpes Simplex Virus Type 1 Reactivates from the Latent State with Reduced Frequency", Journal of Virology, (1989), 63(7): 2893-2900.
Leiva-Torres, et al., "Differential importance of highly conserved residues in UL24 for herpes simplex virus 1 replication in vivo and reactivation", J Gen Virol., (2010), 91: 1109-16.
O'Brien, et al., "Investigation of the Alamar Blue (resazurin) fluorescent dye for the assessment of mammalian cell cytotoxicity", European Journal of Biochemistry, (2000), 267(17): 5421-5426.
Rago, et al., "DNA Fluorometric Assay in 96-Well Tissue Culture Plates Using Hoechst 33258 after Cell Lysis by Freezing in Distilled Water", Analytical Biochemistry, (1990), p. 31-34, vol. 191.
Rani, et al. "Antiviral Activity of Vicoa indica against Herpes Simplex Virus", Indian Journal of Science & Technology, (2013), p. 4683-4686.
Russell, William C., "A Sensitive and Precise Plaque Assay for Herpes Virus", Nature (1962), p. 1028-1029, vol. 195.
Smith, et al., "Age-Specific Prevalence of Infection with Herpes Simplex Virus Types 2 and 1: A Global Review", The Journal of Infectious Diseases, (2002) p. S3-28, vol. 186 (Suppl 1).
Treister et al., "Topical n-docosanol for management of recurrent herpes labialis", Expert Opinion on Pharmacotherapy, (2010), 11(5): 853-860.
Verma, et al., "Antiviral activity of the Indian medicinal plant extract *Swertia chirata* against herpes simplex viruses: a study by in-vitro and molecular approach", Indian J. Med Microbiol, (2008), p. 322-326, vol. 26:4.
Arduino, et al., "Herpes Simplex Virus Type 1 infection: overview on relevant clinico-pathological features" J Oral Pathol Med. (2008), 37(2):107-21.
Bhakuni et al., "New triterpenoid from comus capitata" Indian J Pharm Sci (1988), 50(6): 332-334.
Cunningham et al., "Current management and recommendations for access to antiviral therapy of herpes labialis" (2011) Journal of Clinical Virology, vol. 53, Issue 1, pp. 6-11.
Gottesfeld, "Wet'Suwet'en ethnobotany: Traditional plant uses" (1994) Journal of Ethnobiology 14(2): 185-210.
Hatano et al., "Tannins of cornaceous plants i. comusiins a b and c dimeric monomeric and trimeric hydrolyzable tannins from comus-othcinalis and orientation of valoneoyl group in related tannins" (1989) Chem Pharm Bull (Tokyo) 37(8) :2083-90.
Khan et al., "Occurrence of some antiviral sterols in Artemisia annua" (1991) Plant Sci. 75(2) : 161-165.
Kultur, "Medicinal plants used in Kirklareli Province (Turkey)" (2007) Journal of Ethnopharmacology 111(2): 341-364.
Min, Byung Sun et al., "Inhibitory Effects of Korean Plants on HIV-1 Activities" (2001) Phytotherapy Research 15(6): 481-86.
Tae, Gyun Kim et al., "Screening of some plant extracts for inhibitory activities of hepatitis B virus replication" (1999) Korean Journal of Pharmacognosy 30(3): 238-243.
Nang e al. "Antiviral compounds and one new iridoid glycoside from Comus officinalis" (2006) Progress in Natural Science vol. 16, No. 2, pp. 142-146.
International Preliminary Report on Patentability dated Feb. 4, 2016 in PCT/CA2014/050693.
International Search Report and Written Opinion dated Oct. 16, 2014 in PCT/CA2014/050693.
Wang, CN101049421 English translation by EPO patent translate.
Dharmananda, Comus, Institute for Traditional Medicine, Portland Oregon, May 2003.
Chinese Herbs Healing, Art of herbal Remedies Revealed—Japanese Comelian Cherry (Shan Zhu Yu). Obtained from website (http://www.chineseherbshealing.com/japanese-cornelian-cherry/) on Oct. 31, 2017.

* cited by examiner

USE OF PLANT EXTRACTS AGAINST HERPES SIMPLEX VIRUS

CROSS-REFERENCE TO RELATED APPLICATIONS

This application is a National Entry Application of PCT application Serial No PCT/CA2014/050693 filed on Jul. 22, 2014 and published in English under PCT Article 21(2), which itself claims benefit of U.S. provisional application Ser. No. 61/856,928, filed on Jul. 22, 20142013. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to use of plant extracts against herpes simplex virus (HSV). More specifically, the present invention is concerned with the use of boreal forest plants for inhibiting herpes viruses.

REFERENCE TO SEQUENCE LISTING

N.A.

BACKGROUND OF THE INVENTION

HSV-1's prevalence varies from ~40% for individual younger than about 15 years old and is of about 60-90% in older individuals (Smith and Robinson, 2002). Acyclovir (Greco et al., 2007) and docosanol (Treister and Woo, 2010) are currently used as treatment.

There is a need for alternative treatments for HSV (e.g., HSV-1).

The present description refers to a number of documents, the content of which is herein incorporated by reference in their entirety.

SUMMARY OF THE INVENTION

Various plants, namely an *Achillea* species, namely *Achillea millefolium*, *Cornus* species (i.e., of subgenus *Swida* namely, *C. stolonifera*, of subgenus *Cornus* namely, *C. mas* and of subgenus *Chamaepericlymenum* namely, *C. canadensis*), a *Trillium* species, namely *Trillium erectum*, a *Plantago* species, namely *Plantago major* and a *Trifolium* species, namely *Trifolium repens* have been extracted by decoction, reflux or infusion with water, water/ethanol and/or ethanol. The effects of these extracts have been tested for antiviral activity on herpes simplex virus type-1 (HSV-1) at different courses of the infection including direct effect on the virus, adsorption and virus replication. Results showed that all tested plants possess antiviral activity against HSV-1. *Cornus* species (i.e., of subgenus *Swida* namely, *C. stolonifera*, of subgenus *Cornus* namely, *C. mas* and of subgenus *Chamaepericlymenum* namely, *C. canadensis*) exhibited the highest antiviral activity with $IC_{50}$ values ranging from 25 to 69 μg/ml against HSV-1 replication, and $IC_{50}$ values ranging from 2 to 10 μg/ml against HSV-1 adsorption. The *Achillea*, namely *A. millefolium* leaf was found the most active extract to inhibit directly HSV-1 with an $IC_{50}$ value of 4.8±0.6 μg/ml.

CD-1 mice were infected with herpes simplex virus type-1 (HSV-1) and subsequently treated with an extract from *C. canadensis*. A significant difference was found in clinical disease scores in the group treated with the highest concentration of the extract.

More specifically, in accordance with an aspect the present invention, there is provided a method of using a plant extract for inhibiting an herpes simplex virus (HSV) infection, wherein the plant is: a *Cornus* species (e.g., subgenus *Swida* such as *C. stolonifera*, subgenus *Cornus* such as *C. mas* or subgenus *Chamaepericlymenum* such as *C. canadensis*); an *Achillea* species, e.g., *Achillea millefolium*; a *Trifolium* species, e.g., *Trifolium repens*; a *Trillium* species, e.g., *Trillium erectum*; and/or a *Plantago* species, e.g., *Plantago major*.

In a specific embodiment of the method, the plant is a *Cornus* subgenus *Chamaepericlymenum*. In another specific embodiment of the method, the plant is *Cornus Canadensis*. L. In another specific embodiment of the method, the plant is *Achillea millefolium* L. In another specific embodiment of the method, the plant is *Trifolium repens* L. In another specific embodiment of the method, the plant is *Trillium erectum* L. In another specific embodiment of the method, the plant is *Plantago major* L. The "L." used in association with plants names herein refers to the Carl von Linné's nomenclature. The "L." is however generally omitted from the names herein for concision.

In another specific embodiment of the method, the plant extract is an aqueous, alcoholic or hydroalcoholic extract. In another specific embodiment of the method, the plant extract is an aqueous extract. In another specific embodiment of the method, the plant extract is an alcoholic extract. In another specific embodiment of the method, the alcoholic extract is an ethanolic extract. In another specific embodiment of the method, the plant extract is an hydroalcoholic extract. In another specific embodiment of the method, the plant extract is an hydroethanolic extract. In another specific embodiment of the method, the extract is an infusion. In another specific embodiment of the method, the extract is a decoction. In another specific embodiment of the method, the extract is obtained by reflux. In another specific embodiment of the method, the plant extract is a flower extract. In another specific embodiment of the method, the plant extract is a leaf extract. In another specific embodiment of the method, the plant extract is a stem extract. In another specific embodiment of the method, the HSV is HSV-1.

In another specific embodiment, the method further comprises another agent for inhibiting the herpes simplex virus (HSV) infection (e.g., docosanol).

In accordance with another aspect of the present invention, there is provided an alcoholic or hydroalcoholic extract of *Cornus* subgenus *Chamaepericlymenum* as defined herein.

In accordance with another aspect of the present invention, there is provided an alcoholic or hydroalcoholic extract of *Achillea millefolium* as defined herein.

In accordance with another aspect of the present invention, there is provided an alcoholic or hydroalcoholic extract of *Trifolium repens* as defined herein.

In accordance with another aspect of the present invention, there is provided an alcoholic or hydroalcoholic extract of *Trillium erectum* as defined herein.

In accordance with another aspect of the present invention, there is provided an alcoholic or hydroalcoholic extract of *Plantago major* as defined herein.

In accordance with another aspect of the present invention, there is provided a composition comprising the extract as defined herein, and a pharmaceutically acceptable carrier.

In a specific embodiment, the composition further comprises another agent for inhibiting an herpes simplex virus (HSV) infection (e.g., docosanol).

In accordance with another aspect of the present invention, there is provided a kit for inhibiting an herpes simplex virus (HSV) infection comprising (a) a plant extract as defined herein; and (b) (i) a pharmaceutically acceptable carrier; (ii) another agent for inhibiting an HSV infection (e.g., docosanol); (iii) instructions for using the plant extract for inhibiting an HSV infection; or (iv) any combination of at least two of (i) to (iii).

In accordance with another aspect of the present invention, there is provided a method of using a plant extract or active fraction thereof for inhibiting an herpes simplex virus (HSV) infection or a symptom thereof, wherein the plant is a: (a) *Cornus* species; (b) *Achillea* species; (c) *Trifolium* species; (d) *Trillium* species; and/or (e) *Plantago* species.

In a specific embodiment, the plant is a *Cornus* species. In a more specific embodiment, the plant is a *Cornus* subgenus *Swida*, such as *Cornus stolonifera*; a *Cornus* subgenus *Cornus* such as *Cornus mas*; and/or a *Cornus* subgenus *Chamaepericlymenum* such as *Cornus Canadensis*.

In another specific embodiment, the plant is an *Achillea* species such as an *Achillea millefolium*.

In another specific embodiment, the plant is a *Trifolium* species such as *Trifolium repens*.

In another specific embodiment, the plant is a *Trillium* species such as *Trillium erectum*.

In another specific embodiment, the plant is a *Plantago* species such as *Plantago major*.

In another specific embodiment, the plant extract (or active fraction thereof) is an aqueous, alcoholic or hydroalcoholic extract (or active fraction thereof). In another specific embodiment, the plant extract (or active active fraction thereof) is an aqueous extract (or active fraction thereof). In another specific embodiment, the plant extract (or active fraction thereof) is an alcoholic extract (or active fraction thereof). In another specific embodiment, the alcoholic extract (or active fraction thereof) is an ethanolic extract (or active fraction thereof). In another specific embodiment, the plant extract (or active fraction thereof) is an hydroalcoholic extract (or active fraction thereof). In another specific embodiment, the hydroalcoholic extract (or active fraction thereof) is an hydroethanolic extract (or active fraction thereof). In another specific embodiment, the extract (or active fraction thereof) is an infusion. In another specific embodiment, the extract (or active fraction thereof) is a decoction. In another specific embodiment, the extract (or active fraction thereof) is obtained by reflux. In another specific embodiment, the plant extract or active fraction thereof is a flower extract or active fraction thereof. In another specific embodiment, the plant extract or active fraction thereof is a leaf extract or active fraction thereof. In another specific embodiment, the plant extract or active fraction thereof is a stem extract or active fraction thereof.

In another specific embodiment, the method further comprises using another agent for inhibiting the herpes simplex virus (HSV) infection (e.g., docosanol).

In accordance with another aspect of the present invention, there is provided an alcoholic or hydroalcoholic extract or active fraction thereof of a *Cornus* species as defined herein.

In accordance with another aspect of the present invention, there is provided an alcoholic or hydroalcoholic extract or active fraction thereof of *Achillea* species as defined herein.

In accordance with another aspect of the present invention, there is provided an alcoholic or hydroalcoholic extract or active fraction thereof of *Trifolium* species as defined herein.

In accordance with another aspect of the present invention, there is provided an alcoholic or hydroalcoholic extract or active fraction thereof of *Trillium* species as defined as defined herein.

In accordance with another aspect of the present invention, there is provided an alcoholic or hydroalcoholic extract or active fraction thereof of *Plantago* species as defined herein.

In a specific embodiment, the extract or active fraction thereof as defined herein is for inhibiting an herpes simplex virus (HSV) infection or a symptom thereof. In another specific embodiment of the extract or active fraction thereof, the HSV is HSV-1.

In accordance with another aspect of the present invention, there is provided a composition comprising the extract or active fraction thereof as defined herein.

In another specific embodiment, the composition further comprises an agent for inhibiting an herpes simplex virus (HSV) infection.

The composition of claim 36, further comprising an agent for inhibiting an herpes simplex virus (HSV) infection.

In a specific embodiment, the composition as defined herein is for inhibiting an herpes simplex virus (HSV) infection or a symptom thereof. In another specific embodiment of the composition, the HSV is HSV-1.

In accordance with another aspect of the present invention, there is provided a kit for inhibiting an herpes simplex virus (HSV) infection or a symptom thereof comprising (a) a plant extract or active fraction thereof as defined herein; and (b) (i) a pharmaceutically acceptable carrier; (ii) an agent for inhibiting an HSV infection; (iii) instructions for using the plant extract for inhibiting an HSV infection; or (iv) any combination of at least two of (i) to (iii).

In a specific embodiment of the kit, the HSV is HSV-1.

Advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Extracts

In an embodiment, there are provided extracts or an active fraction thereof from a *Cornus* species plant (whole) or plant part (e.g., flowers, leaves and/or stems). The present invention encompasses extracts from all *Cornus* species including species from subgenuses *Benthamidia, Chamaepericlymenum* (e.g., *Cornus Canadensis*), *Cornus* (e.g., *C. mas*), *Swida* (e.g., *Cornus sericea*) and hybrids thereof. Without being so limited, *Cornus* species encompassed by the present invention are described in Table I below.

Bracts showy but flowers inconspicuous
Flower clusters inconspicuous, usually greenish, but surrounded by large, showy petal-like bracts; fruit usually red:
    Subgenus *Benthamidia* (syn. subgenus *Dendrobenthamia*, subgenus *Cynoxylon*). Flowering
    dogwoods; five species of trees, divisible into two subgroups (*Benthamidia*, with individual
    drupes, and *Dendrobenthamia*, with the drupes coalesced into a compound fruit).
        *Cornus angustata*;
        *Cornus capitata* (*Benthamidia capitata, Dendrobenthamia capitata*; Himalayan Flowering
        Dogwood). Himalaya.
        *Cornus florida* (*Benthamidia florida*; Flowering Dogwood). U.S. east of the Great Plains,
        north to southern Ontario.
        *Cornus hongkongensis* (*Benthamidia hongkongensis, Dendrobenthamia hongkongensis*;
        Hongkong Dogwood). Southern China, Laos, Vietnam.
        *Cornus kousa* (*Benthamidia kousa*, Japanese dogwood, *Dendrobenthamia kousa*; Kousa
        Dogwood). Japan and (as subsp. chinensis) central and northern China.
        *Cornus nuttallii* (*Benthamidia nuttallii*; Pacific Dogwood). Western North America, from
        British Columbia to California.
        *Cornus* × *rutgersensis* (Hybrid: *C. florida* × *C. kousa*). Horticulturally developed.
        *Cornus multinervosa*
    Subgenus *Chamaepericlymenum*. Bunchberries or Dwarf cornels; two species of creeping
    subshrubs growing from woody stolons.
        *Cornus canadensis* (*Chamaepericlymenum canadense*; Canadian Dwarf Cornel,
        Canadian Bunchberry, quatre-temps, crackerberry, creeping dogwood) Northern North
        America, southward in the Appalachian and Rocky Mountains.
        *Cornus suecica* (*Chamaepericlymenum suecicum*; Eurasian Dwarf Cornel or
        Bunchberry). Northern Eurasia, locally in extreme northeast and northwest North
        America.
        *Cornus* × *unalaschkensis* (Hybrid: *C. canadensis* × *C. suecica*). Aleutian Islands
        (Alaska), Greenland, and Labrador and Newfoundland in Canada.
Flowers semi-showy, lacking large bracts
Flower clusters (cymes) semi-showy, usually white or yellow, with surrounding bracts (involucre) either
small and deciduous, or lacking altogether; fruit red, blue, or white:
    Subgenus *Cornus*. Cornels; species of shrubs or small trees; flower clusters with deciduous
    bracts (involucre).
        *Cornus chinensis* (Chinese Cornel). China.
        *Cornus mas* (European Cornel or Cornelian-cherry). Mediterranean.
        *Cornus officinalis* (Japanese Cornel). China, Japan, Korea.
        †*Cornus piggae* (Late Paleocene, North Dakota)
        *Cornus sessilis* (Blackfruit Cornel). California.
        *Cornus eydeana* (from China);
        *Cornus volkensii* (Africa)
    Subgenus *Swida*. Dogwoods; about 20-30 species of shrubs; flower clusters without an
    involucre.
        *Cornus alba* (*Swida alba*; Siberian Dogwood). Siberia and northern China.
        *Cornus alternifolia* (*Swida alternifolia*; Pagoda Dogwood or Alternate-leaf Dogwood).
        Eastern U.S. and southeastern Canada.
        *Cornus amomum* (*Swida amomum*; Silky Dogwood). Eastern U.S. east of the Great
        Plains except for the Deep South.
        *Cornus asperifolia* (*Swida asperifolia*; Toughleaf Dogwood). Southeastern U.S.
        *Cornus austrosinensis* (*Swida austrosinensis*; South China Dogwood). East Asia.
        *Cornus bretschneideri* (*Swida bretschneideri*; Bretschneider's Dogwood). Northern
        China.
        *Cornus controversa* (*Swida controversa*; Table Dogwood, wedding cake tree). East Asia.
        *Cornus coreana* (*Swida coreana*; Korean Dogwood). Northeast Asia.
        *Cornus drummondii* (Here including *C. priceae*; *Swida drummondii*; Roughleaf
        Dogwood). U.S. between the Appalachia and the Great Plains, and southern Ontario,
        Canada.
        *Cornus foemina* (Here including *C. stricta*; *Swida foemina*; Stiff Dogwood) Southeastern
        and southern United States.
        *Cornus glabrata* (*Swida glabrata*; Brown Dogwood or Smooth Dogwood). Western North
        America.
        *Cornus hemsleyi* (*Swida hemsleyi*; Hemsley's Dogwood). Southwest China.
        *Cornus koehneana* (*Swida koehneana*; Koehne's Dogwood). Southwest China.
        *Cornus macrophylla* (*Swida macrophylla*; Large-leafed Dogwood). East Asia. (Chinese:
        梾木; pinyin: jiáliáng or jiàliáng)
        *Cornus obliqua* (*Swida obliqua*; Pale Dogwood). Northeastern and central U.S., and
        southeastern Canada.
        *Cornus paucinervis* (*Swida paucinervis*). China.
        *Cornus racemosa* (*Swida racemosa*; Northern Swamp Dogwood or Gray Dogwood).
        Northeastern and central U.S., and extreme southeastern Canada.
        *Cornus rugosa* (*Swida rugosa*; Round-leaf Dogwood). Northeastern and north-central
        U.S., and southeastern Canada.

*Cornus sanguinea* (*Swida sanguinea*; Common Dogwood). Europe.
*Cornus sericea* (*C. stolonifera*; *Swida sericea*; Red Osier Dogwood). Northern and western North America, except Arctic regions.
*Cornus stricta* (*Swida stricta*; Southern Swamp Dogwood). Southeastern U.S.
*Cornus walteri* (*Swida walteri*; Walter's Dogwood). Central China.
*Cornus wilsoniana* (*Swida wilsoniana*; Wilson's Dogwood). Central China.
*Cornus papillosa*;
*Cornus oblonga*
*Cornus oligophlebia*
*Cornus parviflora*
*Cornus quinquenervis*
*Cornus schindleri*
*Cornus ulotricha*
Hybrids
*Cornus* × *acadiensis*.
*Cornus* × *arnoldiana*.
*Cornus* × *friedlanderi*
*Cornus* × *rutgersensis*
*Cornus* × *slavinii*.
*Cornus* × *unalaschkensis*.

In a more specific embodiment, the *Cornus* species is from subgenus *Chamaepericlymenum, Cornus, Swida* or a hybrid of such species. *C. stolonifera* is a representative species of the *Swida* subgenus, *C. canadensis stolonifera* is a representative species of the *Chamaepericlymenum* subgenus and *C. mas* is a representative species of the *Cornus* subgenus.

In another embodiment, there is provided an extract or an active fraction thereof from an *Achillea* (e.g., *Achillea millefolium* (also called yarrow, common yarrow, plumajillo, gordaldo, nosebleed plant, old man's pepper, devil's nettle, sanguinary, milfoil, soldier's woundwort, thousand-leaf, and thousand-seal), or related species such as *Achillea ageratifolia* and *Achillea nobilis*); a *Trifolium* (e.g., *Trifolium repens* (also called white clover or Dutch clover)); a *Trillium* (e.g., *Trillium erectum* (also known as wake-robin, red trillium, purple trillium, Beth root, or stinking Benjamin)); and/or a *Plantago* (e.g., *Plantago major* (also called broadleaf plantain or greater plantain)) plant (whole) or plant part (e.g., flowers, leaves and/or stems).

The present invention encompasses extracts of single species and extracts of two or more species.

Preparation of Extracts

In accordance with certain embodiments, plants and/or plant parts (e.g., flowers, leaves and/or stems) can be isolated and ground (e.g., coarsely grinded using an electrical blender or mortar and pestle) and/or dried before being powdered/crushed. Other methods known in the art for grinding may be used. The plant material may then be subjected to a solvent extraction process.

In accordance with an embodiment of the invention, plant material (e.g., fresh or dry, crushed or not) may be subjected to a decoction.

As used herein the term "decoction" is meant to refer to a process of extracting by boiling, dissolved chemicals from plant material (e.g., flowers, leaves, stems, roots, bark, rhizomes, etc.). Decoction involves boiling in a solvent (e.g., aqueous solvent, alcoholic solvent, hydroalcoholic solvent, organic solvent, a mix of at least two thereof, etc.) to extract oils, volatile organic compounds, and other chemical substances from the plant.

In an embodiment of the invention, the following decoction procedure may be used: the plant material (e.g., dried plant powder) may be boiled in a solvent (e.g., aqueous solvent, alcoholic solvent, hydroalcoholic solvent, organic solvent, a mix of at least two thereof, etc.) for a time sufficient to extract useful plant components (e.g., about 30 minutes to about 3 hours) and the obtained solution can be filtered. The decoction procedure can be repeated a number of times (e.g., 1, 2, 3, 4, 5 or more) and the result of the successive extractions can be collected and combined.

In accordance with another embodiment of the invention, plant material (e.g., fresh or dried, ground or not) may be subjected to a reflux. As used herein the term "reflux" is meant to refer to a process of extracting chemicals from plant material (e.g., flowers, leaves, stems, roots, bark, rhizomes, etc.) by heating the plant material in a solvent (e.g., aqueous solvent, alcoholic solvent, hydroalcoholic solvent, organic solvent, a mix of at least two thereof, etc.) to create vapors, condensing the vapors and returning this condensate to the mixture of plant and solvent from which it originated. The reflux is a variant of the decoction.

In an embodiment of the invention, the following reflux procedure may be used: Plant material (e.g., fresh or dried, ground or not) may be used. If ground material is used, it may first optionally be sifted with a filter (e.g., 1 to 4 mm mesh). The material (filtrated or not) can be used for the extraction. The plant material can be mixed with a solvent in a container and refluxed for a time sufficient to extract chemicals (e.g., about 30 minutes to about 3 hours) i.e. the mixture can be boiled and the vapor captured in a condenser set up to return the condensed distillate to the container. The mixture can then be filtered, the filtrate recovered and the plant residue left in the container. The reflux procedure may be repeated a number of times (e.g., 1, 2, 3, 4, 5 or more) and the resulting extracts of the successive extractions can be collected and combined. The extracts can be evaporated to remove most alcohol if any (e.g., with a rotary evaporator). The aqueous phase can optionally be diluted with water and then frozen and lyophilized to obtain a powder.

In accordance with another embodiment of the invention, plant material (e.g., fresh or dried, ground or not) may be subjected to an infusion. As used herein the term "infusion" is meant to refer a process of extracting dissolved chemicals from plant material (e.g., flowers, leaves, stems, roots, bark, rhizomes, etc.) in a solvent (e.g., aqueous solvent, alcoholic solvent, hydroalcoholic solvent, organic solvent, a mix of at least two thereof, etc.), by allowing the material to remain suspended in the solvent over time (a process often called steeping).

In an embodiment of the invention, the following infusion procedure may be used: a boiling solvent may be added to the plant material (e.g., fresh or dried, ground or not) and mixed for a time sufficient to extract chemicals (e.g., about 30 minutes to about 3 hours) at a temperature that allows the mixture to cool down (e.g., between about 10° C. and 40° C., preferably between 18° C. and 25° C.). The resulting infusion may be filtered. The infusion procedure can be repeated a number of times (e.g., 1, 2, 3, 4, 5 or more) and the result of the successive extractions can be collected and combined. Crude alcohol extracts may be concentrated under vacuum and subsequently lyophilised. Crude water extracts can be lyophilized.

The solvents that can be used for the extractions procedures (e.g., decoction or infusion or reflux) in accordance with the present invention include water (e.g., distilled and demineralised), hydroalcohol (i.e. mixture water and alcohol (e.g., water/alcohol of more than or about 10%, 20%, 30%, 40%, 50%, 60%, 70%, 80%, 90%), organic solvent, alcohol, or any mixture of at least two of these solvents.

Hydroalcoholic and alcoholic extracts of the present invention may be an ethanolic or methanolic extract, propanolic, butanolic, glycerol, or an extract obtained from a $C_{1-10}$ aliphatic alcohol. In another embodiment, the extracts are obtained using an organic solvent, examples of which include ketones (such as $C_{1-10}$ ketones), hydrocarbons (such as hexane), organic acids, esters (such as ethyl acetate), ethers (such as ethyl ether), alkyl chlorides (such as methylene chloride), etc. A mixture of any two or more (e.g., 3 solvents, 4 solvents, etc.) of the foregoing solvents may be used with or without water (e.g., methanol and ethanol). The first solvent is evaporated to generate a first extract/residue.

Non polar components/impurities. Additional extractions/suspensions may then be carried out to remove non-polar components/impurities of the first extract/residue. This additional extraction is performed with a second solvent (or mixture of solvents) on the first extract/residue obtained with the first solvent (or mixture of solvents). In an embodiment, the first extract/residue obtained with the first solvent (or mixture of solvents) is suspended in ethanol and extracted with an alkane that is non-soluble in methanol (e.g., hexane, pentane, or petroleum ether). The non-polar components/impurities are thus solubilized with the alkane (e.g., hexane) phase which is then discarded. The ethanol phase is then evaporated to generate a second extract/residue.

Polar components/impurities. In an embodiment, the second residue/extract obtained with the second solvent (or mixture of solvents) is subjected to a third suspension/extraction to remove polar components/impurities of the second extract/residue. For instance, the second extract/residue can be suspended in diethyl ether, butanol or chlorinated solvents such as chloroform or chloromethane and extracted with water. In an embodiment, the residue is suspended in $Et_2O$ and extracted with water. The polar components/impurities are thus solubilized with the water phase which is then discarded. The e.g., diethyl ether phase is then evaporated to generate a third extract/residue.

In more specific embodiments, the extract is an ethanolic extract, a methanolic extract, an hydroalcoholic (e.g., hydroethanolic extract) or a water extract of the plants of the present invention in liquid form or dried form. In embodiments, there is provided one or more active fractions obtained by chromatographic separation of each extract of the present invention. Active fractions of the extracts as described herein including in Examples presented herein are encompassed by the present invention.

In embodiments, a preliminary extraction (i.e. prior to the first extraction (e.g., water, hydroalcoholic or alcoholic extraction)) can be performed on the plant material to remove undesirable compounds. For example, hexane or another solvent (e.g., hexane, ether, pentane or petroleum ether) could be used to remove non-polar compounds, such as waxy compounds. The first extraction can then be performed on the cleaned plant material.

In accordance with other embodiments of the present invention, alternatively to the solvent extract process, the extracts of the present invention can also be obtained through the use of supercritical $CO_2$. Supercritical extracts are often referred to as Super Critical Carbon Dioxide Extracts or $SCO_2$, because the process uses compressed carbon dioxide. Carbon dioxide is present in the air and is necessary for plant life. When it is compressed, it can turn into a liquid state. When pressure is increased, temperature increases. The super critical point is the exact temperature and pressure where a gas becomes a liquid. For carbon dioxide, it is relatively low (31 degrees Centigrade). The compressed $CO_2$ at this point has the density of a liquid, but the properties of a gas. The gas-like state helps the faster diffusion of the phytochemicals or extracts—almost two orders of magnitude higher than that of other liquids—while the liquid-like state helps in better solubility of the phytochemicals or extracts. Once the extraction is complete, the pressure is released, and the carbon dioxide is harmlessly freed. The extraction process starts with placing the raw botanical into an extractor. Liquid $CO_2$ is heated to its supercritical state (31 degrees Centigrade), and then pumped into the extractor. The $SCO_2$ then mixes with the botanical. The $SCO_2$, now carrying the desired extract, is transferred to a separator tank where pressure and temperature is controlled. The extract is precipitated in the separator, and $CO_2$ is recycled into the extractor via a condenser.

Combination of extracts prepared according to the same or different procedures from one or more plants (or plant parts) can also be made.

The extract can be in a liquid or dried form.

Plant extracts of the present invention as used in methods of the present invention are preferably non-cytotoxic or used in amounts that are non-cytotoxic against cells of tissues infected by the targeted virus (e.g., HSV). Without being so limited, Table II provides an indication of non-toxic plant extracts. Other non-toxic plant extracts of the present invention may be identified with known methods.

Specific illustrations of extracts of the present invention are described in Examples presented herein. Extracts are described herein may be used in the inhibition of viral infections as described herein.

Methods of Using a Plant Extract of the Present Invention for Inhibiting Herpes Simplex Virus (HSV) Infection Extracts of the invention may be used to treat herpes simplex virus (HSV) infections.

Infection with the HSV is categorized into one of several distinct disorders based on the site of infection. Oral herpes, the visible symptoms of which are colloquially called cold sores or fever blisters, is an infection of the face, throat, eye or mouth. Genital herpes, known simply as herpes, is the second most common form of herpes. HSV-1 causes primarily mouth, throat, face, eye, and central nervous system infections, whereas HSV-2 causes primarily anogenital infections. However, each may cause infections in all areas (Chayavichitsilp et al., 2009).

These infections have various stages and symptoms. Oral HSV infections have the following symptoms. Preliminary signs: tingling, itching, burning, slight swelling/inflammation, redness. Blisters: lip swelling locally (sometimes a large part of the lip swells for a few days before it becomes more localized) and reddening. Wet ulcers: papules become transparent vesicles containing a clear liquid. The vesicles then eventually burst, releasing the liquid. At this time, the virus is released. Dry Crusts (Herpes Scabs): After their breakup, the vesicles often give way to painful wounds (burns) and then dry quickly enough to form crusts that disappear in a few days. Oral herpes lasts 8 to 15 days. The disease is contagious at any time, but even more when the lesions are still present (including in the form of crusts).

The terms "inhibiting" or "treat/treating/treatment" and "prevent/preventing/prevention" as used herein, refers to eliciting the desired biological response, i.e., a therapeutic and prophylactic effect, respectively. In accordance with the subject invention, the inhibition or therapeutic effect comprises one or more of a decrease/reduction in infection or infection symptom, a decrease/reduction in the severity of the infection (e.g., reduction or inhibition of viral adsorption, reduction or inhibition of viral replication, etc.), a decrease/reduction in at least one HSV infection symptom or HSV-related effect (e.g., reduction or inhibition of swelling/inflammation, reduction of redness, reduction of blister or ulcer size, reduction of any symptom duration), an amelioration of symptom or HSV-related effect, and an increased survival time of the affected host animal, following administration of the agent/composition of the invention. In accordance with the invention, an inhibition or prophylactic effect may comprise a complete or partial avoidance/inhibition or a delay of HSV infection or development/progression or a symptom thereof (including a complete or partial avoidance/inhibition or a delay of infection development), and an increased survival time of the affected host animal, following administration of the agent that inhibits HSV infection (or of a composition comprising the agent).

As used herein, "inhibition" of HSV infection or a symptom thereof refers to a reduction in HSV expression or infection or a symptom thereof of at least 10% as compared to expression or replication in a control (a subject not treated with the extract or composition of the present invention), in an embodiment of at least 20% lower, in a further embodiment of at least 30% lower, in a further embodiment of at least 40% lower, in a further embodiment of at least 50% lower, in a further embodiment of at least 60% lower, in a further embodiment of at least 70% lower, in a further embodiment of at least 80% lower, in a further embodiment of at least 90% lower, in a further embodiment of 100% (complete inhibition).

Extracts of the invention also can be administered in combination therapy, i.e., combined with at least one other agent able to inhibit HSV infection. For example, the combination therapy can include an extract of the present invention combined with at least one agent (e.g., plant extract as disclosed herein or other extract).

Medicaments and Pharmaceutical Compositions

The present invention also relates to the use of the above-mentioned extracts in the preparation of a medicament.

The present invention also relates to pharmaceutical compositions comprising the above extracts of the invention.

Without being so limited, the medicaments/pharmaceutical compositions of the invention may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

For the preparation of tablets, coated tablets, dragees or hard gelatin capsules, the dried extracts of the present invention may be admixed with any known pharmaceutically inert, inorganic or organic excipient and/or carrier. Examples of suitable excipients/carriers include lactose, maize starch or derivatives thereof, talc or stearic acid or salts thereof.

As used herein the terms "subject in need thereof" refer to a subject who would benefit from receiving an effective amount of the extract of the present invention. It refers to an animal and to a human in a specific embodiment. The extracts of the present invention may also be used for veterinary applications and be used in pets or other animals (e.g., pets such as cats, dogs, horses, etc.; and cattle, fishes, swine, poultry, etc.).

Suitable excipients for use with soft gelatin capsules include for example vegetable oils, waxes, fats, semi-solid or liquid polyols etc. According to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, saline, alcohols, polyols, glycerine, vegetable oils and other appropriate excipients.

For suppositories, and local or percutaneous application, excipients which may be used include for example natural or hardened oils, waxes, fats and semi-solid or liquid polyols.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Topical or oral administrations are preferred forms of use. The dosages in which the extracts of the invention are administered in effective amounts depend on the nature of the specific active ingredient, the age and the requirements of the patient and the mode of application.

As mentioned above, the pharmaceutical compositions of the invention can contain a pharmaceutically acceptable carrier including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

The extracts of the invention may be incorporated into dosage forms in conjunction with any of the vehicles which are commonly employed in pharmaceutical preparations, e.g., talc, gum arabic, lactose, starch, magnesium searate, cocoa butter, aqueous or non-aqueous solvents, oils, paraffin derivatives or glycols. Emulsions such as those described in U.S. Pat. No. 5,434,183, incorporated herein by reference, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa. incorporated herein by reference).

In cases where parenteral administration is elected as the route of administration, preparations containing the extracts of the invention may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

It is a prerequisite that all adjuvants used in the manufacture of the preparations, such as carriers, are non-toxic and more generally pharmaceutically acceptable.

As used herein, "pharmaceutically acceptable" such as pharmaceutically acceptable carrier, excipient, etc., means pharmacologically acceptable and substantially non-toxic to the subject to which the particular extract is administered.

Any amount of a pharmaceutical composition can be administered to a subject. The dosages will depend on many factors including the mode of administration. Typically, the amount of the extract of the invention contained within a single dose will be an amount that effectively prevent, delay or treat the disease or condition to be treated, delayed or prevented without inducing significant toxicity.

The effective amount of the extracts of the invention may also be measured directly. The effective amount may be given daily or weekly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced.

The present invention also relates to the use of the above-mentioned medicament for treating viral infections in humans and animals (e.g., cats, dogs, horses, cattle, swine, etc.).

As used herein, "viral infection" means an infection caused by a virus (e.g., HSV-1, HSV-2).

The use of the terms "a" and an and the and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

The present invention is illustrated in further details by the following non-limiting examples.

Example 1

Materials and Methods

Cell Culture and Viruses

African green monkey kidney cells (Vero, ATCC CCL-81) were obtained from the American Type Culture Collection (ATCC, Manassas, USA). The Vero cell line were grown in Eagle's minimal essential medium (MEM) (Mediatech Cellgro, Va.) supplemented with 10% fetal bovine serum (FBS; Hyclone, Logan, USA), penicillin (100 IU) and streptomycin (100 µg/ml) (Mediatech Cellgro™). Cells were cultured in a humidified atmosphere at 37° C. in 5% $CO_2$. The maintenance medium components were similar to growth medium except that they contained only 2% of FBS. HSV-1 (ATCC VR-733) stocks were propagated on Vero cells and stored at −80° C. before further analysis. The virus titer was determined by plaque assay (Russell, 1962).

Plants Collection and Extraction

The *Achillea millefolium, Cornus canadensis, Trillium erectum, Plantago* major *Trifolium repens* specimens were harvested between May and July 2008 in the Simoncouche forest of the Réserve faunique des Laurentides, Quebec (48° 13' 59" N-71° 14' 59" W), Canada. *Cornus mas* specimens were harvested in Drakčići, near the town of Kraljevo, in Serbia, in June 2011. *Cornus stolonifera* specimens were harvested in Laterriere a sector of Chicoutimi, Quebec in or around September 2013.

Leaves, flowers and stems were separated, and dried at room temperature before being powdered/crushed. Three types of extraction were then performed.

Decoction: Powdered plants (10 g) were boiled in 100 ml of solvent (i.e. water, hydroalcoholic (EtOH 50%) or alcoholic (EtOH 100%)) for one hour and the obtained decoction was filtered. The same procedure was repeated three times and the result of the three successive extractions was collected and combined.

Infusion: A boiling solvent (i.e. water, hydroalcoholic (EtOH 50%) or alcoholic (EtOH 100%)) was added to 10 g of powdered plants and mixed for one hour at room temperature, the resulting infusion was filtered and the procedure was repeated three times as described above. Distilled and demineralised water, 50% ethanol and 100% ethanol were the solvents. Crude ethanol extracts were concentrated under vacuum and subsequently lyophilised while crude water extracts were only lyophilized.

Refluxing: Powdered plants were sifted with a 2.3 mm mesh filter. 1 g of filtrated powder was used for the extraction. 1. The plant powder was mixed either with 16 ml of a hydroalcoholic solvent: mixture $H_2O$:EtOH 50:50 to produce the hydroethanolic extract or ETOH 100% to produce the ethanolic extract in a 50 mL flask. For the *C. stononifera*, 10 g of ground plant was mixed with 100 mL of ETOH/water 50:50. 2. The mixture was then refluxed for 1 h i.e. the mixture was boiled and the vapor was captured in a condenser set up to continuously return the condensed distillate to the flask. 3. The mixture was then filtered, the filtrate recovered and the plant residue left in the flask. 4. Steps 1-3 were repeated two more times on the plant residue, using 10 mL of solvent. 5. The three solutions were combined and evaporated to remove most of the ethanol with a rotary evaporator. 6. The aqueous phase was diluted with 20 ml of water and then frozen at −18° C. The extract was lyophilized to obtain a powder.

Cytotoxicity Assay

Exponentially growing cells were plated at a density of $15 \times 10^3$ cells per well in 96-well microplates (Costar, Corning Inc.) in 100 µl of culture medium and were allowed to adhere for 16 h for Vero cells before treatment. Then, 100 µl of increasing concentrations of extract dissolved in DMSO (Sigma-Aldrich) were added. The final concentration of solvent in the culture medium was maintained at 0.25% (v/v) to avoid solvent toxicity. The cells were incubated for 72 h for Vero cells with or without the extract. Cytotoxicity was assessed using the resazurin reduction test (O'Brien et al., 2000). Fluorescence was measured using an automated 96-well Fluoroskan™ Ascent Fl™ plate reader (Labsystems) at excitation and emission wavelengths of 530 and 590 nm respectively. Fluorescence was proportional to the cellular metabolic activity in each well. After reading the resazurin test, cells were prepared for cellular DNA assay with Hoechst dye 33342. After a rinse with PBS solution, cells were dried and kept at −80° C. until the Hoechst assay was carried out (Rago et al., 1990). Cytotoxicity was measured as the concentration of extract or compound inhibiting cell growth by 50% ($IC_{50}$).

Antiviral activity of extracts against herpes simplex type-1 virus

Plaque assays were performed with monolayer cultures of Vero cells in 24-well culture plates. For plaque reduction assay, cell monolayer was infected with virus (30 pfu/well) and incubated at 37° C. with 5% $CO_2$ for one hour. The infected cell monolayer was then washed with PBS and overlaid with overlapping solution (maintenance medium containing 1% methylcellulose and various concentrations of indicated compounds). After 72 h of incubation at 37° C., cell monolayer was fixed with 5% paraformaldehyde and stained with 0.8% crystal violet. Plaques were counted and the percentage of inhibition was calculated as $[(P_c-P_e)/P_c]$ 100, where $P_c$ and $P_e$ refer to the plaque number in the absence and presence of the compound, respectively. The minimal concentration of compounds required to reduce 50% of plaque numbers ($IC_{50}$) was also calculated.

Mode of Antiviral Activity

Cells and viruses (HSV-1) were incubated with acyclovir and various extracts at different stages during the viral infection cycle in order to determine the antiviral action mode (Koch et al., 2008). (A) For virus pretreatment assay, the virus suspension was incubated in a medium containing different concentrations of the extracts for one hour at 37° C. prior to infection of Vero cells. (B) The cell pretreatment assay was performed with cell monolayers that were pretreated with the extracts or positive control acyclovir for 1 hour at 37° C. prior to virus inoculation. (C) For analysing the antiviral inhibition during the adsorption period, HSV-1 was mixed with the drug and immediately added to the cells, incubated for 1 hour at 37° C. and then treated as described for resazurin reduction and lysis plaques assay. (D) The effect of extracts during the replication period was tested by adding the compounds to the overlay medium after the infection.

Statistical Analysis

All experiments were performed in triplicate for HSV-1. A one-way ANOVA with a Tukey's multiple comparison test was performed to compare extracts with negative control for the antiviral assay. Statistical significance was set at $p<0.05$.

Example 2

Extraction Yield

Plants flower, leaf or stem were extracted using decoction and infusion. Flower, leaf and stem of *Achillea millefolium, Cornus canadensis, C. stolonifera, Trillium erectum, Plantago major* and *Trifolium repens* were extracted with water, ethanol and/or equal volume of water/ethanol. Table II below presents the extraction yield of the extracts. The extraction yield varies from 6.4 to 56.1%. Generally, the highest yields were obtained with water and the lowest with ethanol. Overall, no significant difference was observed between decoction and infusion methods except for water extract of flower of *C. canadensis*. Indeed, water decoction (yield of 56%) was more efficient compare to infusion (yield of 25%).

To determine extracts safety, their in vitro cytotoxicity on culture cells was evaluated as also shown in Table II.

Example 3

Extracts Cytotoxicity on VERO Cells

Extracts cytotoxicity was assessed on cell lines used to evaluate the antiviral activity: namely VERO cells. Both cell lines were incubated in the presence or in the absence of a growing concentration of extract over three days for VERO cells. The results, as shown on Table II, are expressed as the concentration inhibiting fifty percent of cell growth ($IC_{50}$). The results show that none of the *P. major* and *T. repens* extracts were cytotoxic ($IC_{50}>100$ µg/ml) against the cell line. *T. erectum* water/ethanol flower extract was found weakly cytotoxic against VERO cells with $IC_{50}$ of 62 µg/ml. None of the *C. canadensis* extracts were cytotoxic against VERO cells. None of the *A. millefolium* stem extracts, or leaf or flower water extracts were cytotoxic against VERO cells. None of the *C. stolonifera* and *C. mas* extracts were cytotoxic ($IC_{50}$>200 μg/ml) against the cell line. *A. millefolium* ethanolic flower and leaf extracts inhibited cell growth of VERO cells with $IC_{50}$ ranging from 25 to 80 μg/ml.

TABLE II

Extraction yield (%) and cytotoxicity of extracts from *A. millefolium*, *C. canadensis*, *C. stolonifera*, *C. mas*, *T. erectum*, *P. major* and *T. repens* on Vero cell lines.

| Plant | Extraction | Solvent | Extraction yield (%) | $IC_{50}$ (μg/ml)[1] Vero |
|---|---|---|---|---|
| *Achillea millefolium* | | | | |
| flower | decoction | Water | 25.5 | >100 |
| | | EtOH 50% | 23.1 | >100 |
| | | EtOH 100% | 16.4 | 54 ± 2 |
| | infusion | Water | 21 | >100 |
| | | EtOH 50% | 20.1 | 76 ± 13 |
| | | EtOH 100% | 13.3 | 25 ± 2 |
| leaf | decoction | Water | 32.8 | >100 |
| | | EtOH 50% | 28.8 | >100 |
| | | EtOH 100% | 11.4 | 67 ± 7 |
| | infusion | Water | 24.2 | >100 |
| | | EtOH 50% | 22.2 | >100 |
| | | ETOH 100% | 8.2 | 80 ± 7 |
| stem | decoction | Water | 21.6 | >100 |
| | | EtOH 50% | 19.7 | >100 |
| | | EtOH 100% | 8.7 | >100 |
| | infusion | Water | 21.2 | >100 |
| | | EtOH 100% | 6.4 | >100 |
| | | EtOH 50% | 17 | >100 |
| *Cornus canadensis* | | | | |
| flower | decoction | Water | 56.1 | >100 |
| | | EtOH 50% | 39.6 | >100 |
| | | EtOH 100% | nd | nd |
| | infusion | Water | 24.6 | >100 |
| | | EtOH 50% | 39 | >100 |
| | | EtOH 100% | nd | nd |
| leaf | decoction | Water | 36.5 | >100 |
| | | EtOH 50% | 34.1 | >100 |
| | | EtOH 100% | 18 | >100 |
| | infusion | Water | 30.1 | >100 |
| | | EtOH 50% | 34.3 | >100 |
| | | EtOH 100% | 12.2 | 88 ± 18 |
| stem | decoction | Water | 27.7 | >100 |
| | | EtOH 50% | 21.5 | >100 |
| | | EtOH 100% | 12.4 | >100 |
| | infusion | Water | 34.4 | >100 |
| | | EtOH 50% | 23.1 | >100 |
| | | EtOH 100% | 7.5 | >100 |
| *Cornus stolonifera* | | | | |
| leaf | reflux | EtOH 50% | nd | >200 |
| stem | reflux | EtOH 50% | 11 | >200 |
| *Cornus Mas* | | | | |
| leaf | reflux | EtOH 50% | nd | >200 |
| | reflux | EtOH 100% | nd | >200 |
| *Trillium erectum* | | | | |
| flower | decoction | Water | 46.7 | >100 |
| | | EtOH 50% | 46.5 | 82 ± 12 |
| | | EtOH 100% | nd | nd |
| | infusion | Water | 44.1 | >100 |
| | | EtOH 50% | 40 | 62 ± 9 |
| | | EtOH 100% | nd | nd |
| leaf | decoction | Water | 47.5 | >100 |
| | | EtOH 50% | 38 | >100 |
| | | EtOH 100% | 27 | >100 |
| | infusion | Water | 42.3 | >100 |
| | | EtOH 50% | 41.9 | >100 |
| | | EtOH 100% | 18.1 | >100 |
| stem | decoction | Water | 46.8 | 73 ± 20 |
| | | EtOH 50% | 44.3 | >100 |
| | | EtOH 100% | 23.7 | >100 |
| | infusion | Water | N/A | >100 |
| | | EtOH 50% | nd | nd |
| | | EtOH 100% | 15.1 | >100 |
| *Plantago major* | | | | |
| leaf | decoction | Water | 43.2 | >100 |
| | | EtOH 50% | 31.1 | >100 |
| | | EtOH 100% | 18.8 | >100 |
| | infusion | Water | 37.6 | >100 |
| | | EtOH 50% | 29 | >100 |
| | | EtOH 100% | 9.9 | >100 |
| stem | decoction | Water | 28.4 | >100 |
| | | EtOH 50% | 17.3 | >100 |
| | | EtOH 100% | 13.3 | >100 |
| | infusion | Water | 18.3 | >100 |
| | | EtOH 50% | 19.3 | >100 |
| | | EtOH 100% | 7.5 | >100 |
| *Trifolium repens* | | | | |
| flower | decoction | Water | 30.9 | >100 |
| | | EtOH 50% | 29.3 | >100 |
| | | EtOH 100% | 20.3 | >100 |
| | infusion | Water | 26.4 | >100 |
| | | EtOH 50% | 29.2 | >100 |
| | | EtOH 100% | 16.6 | >100 |
| stem | decoction | Water | 32.5 | >100 |
| | | EtOH 50% | 34 | >100 |
| | | EtOH 100% | 20.3 | >100 |
| | infusion | Water | 31.1 | >100 |
| | | EtOH 50% | 31.6 | >100 |
| | | EtOH 100% | 16.1 | >100 |

[1]Concentration inhibiting 50% of cell growth.
nd—not determined.

Example 4

Extracts Antiviral Activity Against Herpes Virus Type-1

The antiviral activity of non-cytotoxic plant extracts was determined against HSV-1 in vitro. To determine the mechanism of action of the extracts, the virus was added at different stages of the infection. In order to evaluate direct extract effect, the virus (method A) was pre-treated with extracts (100 μg/ml) for one hour before the VERO cells infection. To evaluate the effect of extract on virus adsorption, cells were pre-treated for 1 hour without virus (method B) and with virus (method C) before washing. Finally, to assess the virus replication effect, the extracts were added after VERO infection and the cells were incubated in the presence of extract over a period of four days (method D). Then, the cells were washed and quantified using resazurin.

The results are shown in Table III below and were expressed as the percentage of inhibition of lysis plaques compared with untreated infected cells controls. Acyclovir was used as positive control: a dose of 0.75 μg/ml protects VERO cells against infection.

All the tested plants exhibited an antiviral activity by acting directly, blocking the adsorption of the virus and its replication.

Decoction water/ethanol of flower, leaf and stem of *A. millefolium* achieved a protection (method A) of 95, 100 and 92%, respectively. Decoction of *A. millefolium* leaf with water, water/ethanol and ethanol strongly inhibited adsorption of virus with 80, 100 and 85% protection, respectively. The *A. millefolium* leaf extract was moderately active against the replication of virus with a protection of about 50%.

*C. canadensis*' flower and leaf extracts interacted directly (method A) with HSV-1 to inhibit 100% of virus infection. *C. canadensis*' stem extracts also directly affected HSV-1 to inhibit between 81% and 100% of virus infection. *C. canadensis*' flower and leaf extracts strongly protected against virus adsorption (method C) with inhibitions ranging from 90% to 100%. *C. canadensis*' leaf extracts strongly protected VERO cells against virus replication (method D) with an inhibition ranging from 69 to 100%. Certain *C. canadensis*' stem extracts also protected against virus adsorption or replication with inhibitions ranging from 43% to 100%. All *C. mas* and *C. stolonifera* extracts inhibited 100% of HSV-1 infections (methods A and C, and A, C and D, respectively).

*T. erectum*'s flower infusion extracts with water and water/ethanol inhibited, respectively, the virus replication (46% of inhibition) or virus adsorption (79% of inhibition). *T. erectum*'s leaf infusion extracts with water/ethanol or ethanol protected the cells against infection by a direct effect on HSV-1 (73% and 66% of inhibition, respectively).

*P. major*'s best antiviral activity was observed with ethanol and water/ethanol leaf and stem extracts with inhibitions ranging from about 73% to about 100%.

*T. repens*' flower and stem extracts protected the VERO cells infection by acting directly on HSV-1 with inhibitions ranging from about 29% to about 97%.

TABLE III

Antiviral effect of specific concentration of *A. millefolium*, *Cornus* species, (i.e. *C. canadensis* and *C. mas*), *T. erectum*, *P. major* and *T. repens* Extracts against HSV-1. Results are given in percentage of inhibition of lysis plaques compared with untreated infected cells controls.

| Plant/Plant part | Extraction type | Solvent | Inhibitory percentage of lysis plaques (at 100 μg/ml) | | | |
|---|---|---|---|---|---|---|
| | | | A | B | C | D |
| Acyclovir (positive control) | — | — | NA | NA | NA | 100 |
| *Achillea millefolium* | | | | | | |
| flower | decoction | Water | 63 ± 9 | NA | NA | NA |
| | | EtOH 50% | 95 ± 9 | NA | 49 ± 27 | NA |
| | | EtOH 100% | 93 ± 23 | NA | 47 ± 12 | Tx |
| | infusion | Water | 59 ± 14 | NA | NA | NA |
| | | EtOH 50% | NA | NA | NA | Tx |
| | | EtOH 100% | NA | NA | NA | Tx |
| leaf | decoction | Water | 96 ± 4 | NA | 80 ± 7 | 53 ± 10 |
| | | EtOH 50% | 100 | NA | 100 | 42 ± 16 |
| | | EtOH 100% | NA | NA | 85 ± 7 | Tx |
| | infusion | Water | 84 ± 5 | NA | NA | NA |
| | | EtOH 50% | 100 | NA | 67 ± 8 | 54 ± 13 |
| | | EtOH 100% | 96 ± 4 | NA | NA | *** |
| stem | decoction | Water | 84 ± 14 | NA | NA | NA |
| | | EtOH 50% | 92 ± 8 | NA | 56 ± 13 | NA |
| | | EtOH 100% | NA | NA | 43 ± 21 | NA |
| | infusion | Water | 95 ± 7 | NA | NA | NA |
| | | EtOH 50% | 72 ± 24 | NA | NA | 27 ± 16 |
| | | EtOH 100% | NA | NA | NA | NA |
| *Cornus canadensis* | | | | | | |
| flower | decoction | Water | 100 | NA | 96 ± 6 | NA |
| | | EtOH 50% | 100 | NA | 100 | NA |
| | | EtOH 100% | nd | nd | nd | nd |
| | infusion | Water | 100 | NA | 93 ± 6 | NA |
| | | EtOH 50% | 100 | NA | 97 ± 3 | 69 ± 14 |
| | | EtOH 100% | nd | nd | nd | nd |
| leaf | decoction | Water | 100 | NA | 100 | 69 ± 11 |
| | | EtOH 50% | 100 | NA | 99 ± 2 | 94 ± 4 |
| | | EtOH 100% | 100 | NA | 90 ± 0 | 91 ± 16 |
| | infusion | Water | 100 | NA | 99 ± 2 | 85 ± 7 |
| | | EtOH 50% | 100 | NA | 98 ± 4 | 82 ± 10 |
| | | EtOH 100% | 100 | NA | 100 | 100 |
| stem | decoction | Water | 100 | NA | NA | NA |
| | | EtOH 50% | 100 | NA | 97 ± 5 | NA |
| | | EtOH 100% | NA | NA | 43 ± 15 | 55 ± 21 |
| | infusion | Water | 100 | NA | 100 | NA |
| | | EtOH 50% | 91 ± 9 | NA | NA | 43 ± 4 |
| | | EtOH 100% | 81 ± 22 | NA | 72 ± 35 | NA |
| *Cornus stolonifera* | | | | | | |
| Leaf | Reflux | EtOH 50% | 100 | Nd | 100 | 100 |
| Stem | Reflux | EtOH 50% | 100 | Nd | 100 | 100 |

TABLE III-continued

Antiviral effect of specific concentration of *A. millefolium*, *Cornus* species, (i.e. *C. canadensis* and *C. mas*), *T. erectum*, *P. major* and *T. repens* Extracts against HSV-1. Results are given in percentage of inhibition of lysis plaques compared with untreated infected cells controls.

| Plant/Plant part | Extraction type | Solvent | Inhibitory percentage of lysis plaques (at 100 μg/ml) | | | |
|---|---|---|---|---|---|---|
| | | | A | B | C | D |
| *Cornus mas* | | | | | | |
| Leaf | Reflux | EtOH 50% | 100 | NA | 100 | NA |
| | Reflux | EtOH 100% | 100 | NA | 100 | NA |
| *Trillium erectum* | | | | | | |
| flower | decoction | Water | NA | NA | NA | NA |
| | | EtOH 50% | NA | NA | NA | Tx |
| | | EtOH 100% | nd | nd | nd | Nd |
| | infusion | Water | NA | NA | NA | 46 ± 9 |
| | | EtOH 50% | 52 ± 19 | NA | 79 ± 6 | Tx |
| | | EtOH 100% | nd | nd | nd | Nd |
| leaf | decoction | Water | NA | NA | NA | NA |
| | | EtOH 50% | NA | NA | NA | NA |
| | | EtOH 100% | NA | NA | 57 ± 19 | NA |
| | infusion | Water | NA | NA | NA | NA |
| | | EtOH 50% | 73 ± 6 | NA | NA | NA |
| | | EtOH 100% | 66 ± 4 | NA | NA | NA |
| stem | decoction | Water | NA | NA | NA | Tx |
| | | EtOH 50% | NA | NA | NA | NA |
| | | EtOH 100% | NA | NA | NA | NA |
| | infusion | Water | NA | NA | NA | NA |
| | | EtOH 50% | nd | nd | nd | nd |
| | | EtOH 100% | NA | NA | NA | NA |
| *Plantago major* | | | | | | |
| leaf | decoction | Water | NA | NA | NA | NA |
| | | EtOH 50% | NA | NA | NA | NA |
| | | EtOH 100% | 89 ± 18 | NA | NA | NA |
| | infusion | Water | NA | NA | NA | NA |
| | | EtOH 50% | 73 ± 13 | NA | NA | 39 ± 18 |
| | | EtOH 100% | 100 | NA | NA | NA |
| stem | decoction | Water | NA | NA | NA | NA |
| | | EtOH 50% | 85 ± 8 | NA | NA | NA |
| | | EtOH 100% | NA | NA | 62 ± 25 | NA |
| | infusion | Water | NA | NA | NA | NA |
| | | EtOH 50% | NA | NA | NA | NA |
| | | EtOH 100% | NA | NA | NA | 79 ± 9 |
| *Trifolium repens* | | | | | | |
| flower | decoction | Water | 89 ± 5 | NA | NA | NA |
| | | EtOH 50% | 89 ± 10 | NA | NA | NA |
| | | EtOH 100% | 74 ± 24 | NA | 43 ± 12 | NA |
| | infusion | Water | 29 ± 4 | NA | NA | NA |
| | | EtOH 50% | NA | NA | NA | NA |
| | | EtOH 100% | 97 ± 5 | NA | NA | NA |
| stem | decoction | Water | NA | NA | NA | NA |
| | | EtOH 50% | NA | NA | NA | NA |
| | | EtOH 100% | NA | NA | NA | NA |
| | infusion | Water | NA | NA | NA | NA |
| | | EtOH 50% | NA | NA | NA | NA |
| | | EtOH 100% | 83 ± 8 | NA | NA | NA |

A—Activity when viruses were pre-treated with extract before infection.
B—Activity when cells were pre-treated with extract before infection.
C—Activity during the adsorption period (extracts were added during infection and the wash).
D—Activity during the replication period (extracts were added after infection and stay 3 days on cells).
NA—Not Active.
Tx—These extracts could not be tested at 100 μg/ml with method D due to cytotoxicity.
nd—not determined.

Example 5

IC$_{50}$ Values

The IC$_{50}$ concentration was evaluated to identify the best extracts at each infection stage.

Table IV below shows that the *Cornus* species displayed the best activities overall. *C. stolonifera* displayed the highest antiviral activity in terms of inhibition of virus adsorption with an IC$_{50}$ of 2 μg/ml (method C) and in terms of HSV-1 replication inhibition with an IC$_{50}$ of 25 μg/ml to 42 μg/ml (method D). *C. canadensis*' flower and leaf water decoction and leaf water/ethanol infusion inhibited virus adsorption (method C) with IC$_{50}$ values ranging from 9 to 10 μg/ml. For HSV-1 replication inhibition (method D), *C. canadensis*' extracts exhibited IC$_{50}$ values ranging from 44 to 69 μg/ml. *A. millefolium*'s leaf water/ethanol decoction was the most active extract to inhibit directly HSV-1 (method A) with an IC$_{50}$ of 4.8±0.6 μg/ml. While *C. mas*' ability to reduce HSV-1 plaques was not tested at concentrations lower than 100 μg/ml, its IC$_{50}$ is expected to be much lower since at 100 μg/ml, it was able to inhibit 100% of lysis plaques (see Table III).

TABLE IV

Extracts concentrations reducing HSV-1 lysis plaques by 50% of more.

| Plant/Plant part | Extraction type | Solvent | IC$_{50}$ (μg/ml)[1] A | B | C | D |
|---|---|---|---|---|---|---|
| *Achillea millefolium* | | | | | | |
| leaf | decoction | EtOH 50% | 4.8 ± 0.6 | NA | 45 ± 7 | NA |
| stem | decoction | Water | 20 ± 6 | NA | 36 ± 1 | NA |
| *Cornus canadensis* | | | | | | |
| flower | decoction | Water | 6.0 ± 0.9 | NA | 10 ± 3 | NA |
|  |  | EtOH 50% | 16 ± 4 | NA | 30 ± 5 | NA |
|  | infusion | Water | 31 ± 3 | NA | 94 ± 16 | NA |
|  |  | EtOH 50% | 25 ± 5 | NA | 29 ± 6 | NA |
| leaf | decoction | Water | 17 ± 6 | NA | 9 ± 1 | 69 ± 18 |
|  |  | EtOH 50% | 14 ± 4 | NA | 31 ± 5 | 44 ± 8 |
|  |  | EtOH 100% | 22 ± 3 | NA | 44 ± 8 | 61 ± 3 |
|  | infusion | Water | 14 ± 3 | NA | 17 ± 2 | NA |
|  |  | EtOH 50% | 11 ± 2 | NA | 9 ± 3 | 51 ± 8 |
|  |  | EtOH 100% | 28 ± 6 | NA | 40 ± 5 | 67 ± 24 |
| stem | decoction | Water | 15 ± 4 | NA | 54 ± 9 | 50 ± 19 |
|  |  | EtOH 50% | 8 ± 3 | NA | 36 ± 9 | NA |
|  | infusion | Water | 16 ± 2 | NA | 39 ± 8 | NA |
| *Cornus stolonifera* | | | | | | |
| Leaf | Reflux | EtOH 50% | 9 ± 2 | 109 ± 26 | 2 ± 3 | 42 ± 3 |
| Stem | Reflux | EtOH 50% | 7 ± 1 | 83 ± 20 | 2 ± 4 | 25 ± 3 |
| *Cornus mas* | | | | | | |
| Leaf | Reflux | EtOH 50% | <100 | NA | <100 | NA |
|  | Reflux | EtOH 100% | <100 | NA | <100 | NA |
| *Plantago major* | | | | | | |
| stem | decoction | ETOH 100% | 60 ± 17 | NA | NA | NA |

A—Activity when viruses were pre-treated with extract before infection.
B—Activity when cells were pre-treated with extract before infection.
C—Activity during the adsorption period (extracts were added during infection and the wash).
D—Activity during the replication period (extracts were added after infection and stay 3 days on cells).
N.A.—Not Active.

Example 6

Preparations and Activity of Plant Extract Fractions

Extracts as described above (Example 1) are subjected to column chromatography on with suitable solvents. Eluents are collected separately to obtain various fractions. More particularly, after evaporation of EtOH, the stem and leaf extract (($H_2O$:EtOH 50:50) of *C. canadensis* was partitioned with $CHCl_3$. Both layer were separated and evaporated in vacuo yielding a green $CHCl_3$ fraction and a brown aqueous fraction. The brown gum was suspended in water and extracted with n-BuOH. Both fractions were evaporated in vacuo yielding a brown water fraction and a brown n-BuOH fraction. The n-BuOH fraction was separated by CC on Diaïon with a step gradient of $H_2O$ and MeOH as follow: $H_2O$ and MeOH 10% afforded fractions F1 and F2, MeOH 30 to 50% afforded fractions F3 and F4, MeOH 80% afforded fraction F5 and MeOH 100% afforded fraction F6. Fraction F4 was separated by LPLC on silica gel with DCM-MeOH—$H_2O$ (200:48:7→40:48:7) as eluent followed by MeOH containing 2% acetic acid. The fractions obtained were grouped according to TLC similarity providing seven fractions: F4.1, F4.2, F4.3, F4.4, F4.5, F4.6, F4.7. Fraction F5 was separated by CC on silica gel with DCM-MeOH (6:1→0:1) affording ten fractions: F5.1, F5.2, F5.3, F5.4, F5.5, F5.6, F5.7, F5.8, F5.9, F5.10.

Figure 3:
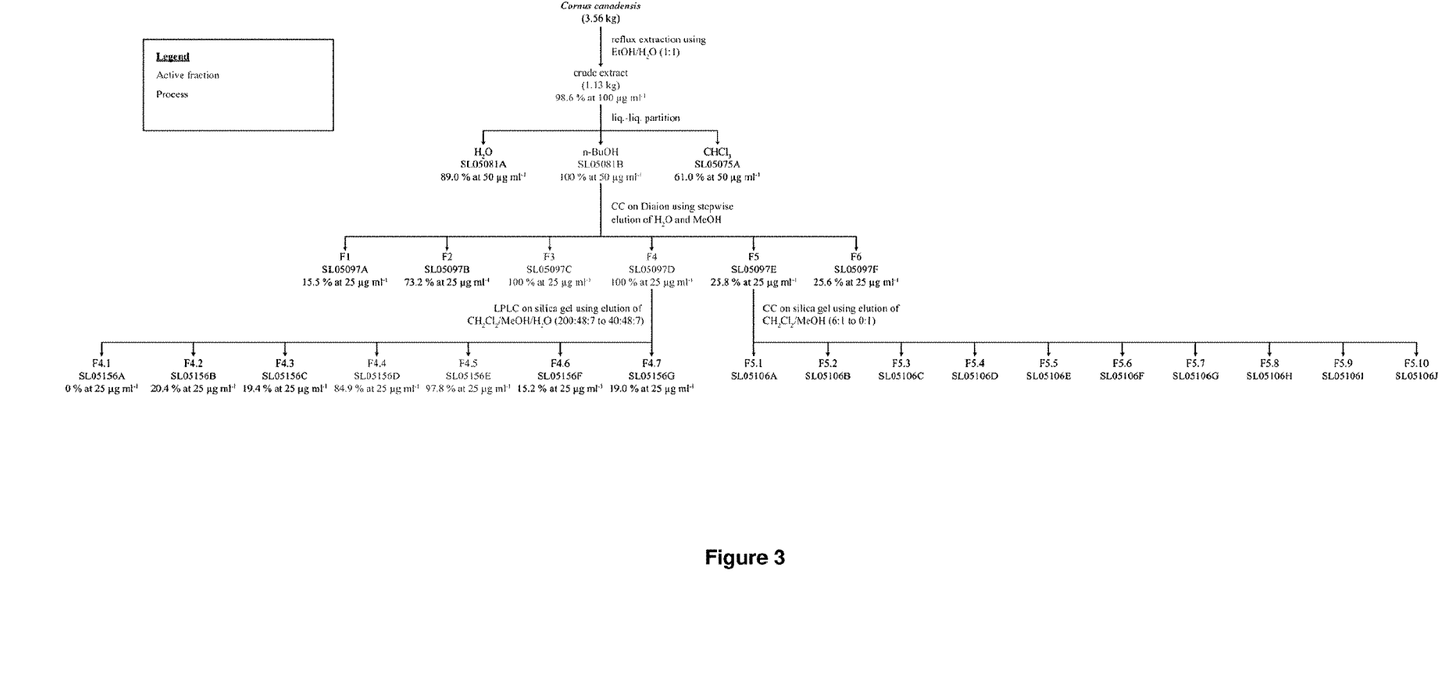
FIG. 3 presents schematically fractions obtained in Example 6 of *C. canadensis* leaf and stem water:EtOH 50:50 extracts and their anti-HSV activity.

Fractions were further investigated in assays as described in Examples 2-5 and various fractions (e.g., $H_2O$ (SL5081A), n-BuOH, F2, F3, F4, F4.4, F4.5) were shown to display anti-HSV-1 activity (active fractions) as presented in FIG. 3.

Example 7

Study of Antiviral Activity of a *Cornus Canadensis* Extract in a Mouse Model of Herpes Simplex Virus Infection Hydroethanolic extracts ($H_2O$:EtOH 50:50) obtained from refluxing *C. canadensis* as described in Example 1 were used. 2.5 mg/ml, 5 mg/ml and 10 mg/ml of the extract were mixed in a solution of 0.5% (v/v) ethanol in PBS.

An eye infection model was used wherein mice eyes are infected following light scarification (Coen et al, 1989; Jocobson et al., 1998; Leib et al., 1989; and Leiva-Torres, 2010). Inflammation occurs at day 4 post-infection (dpi) and increases in the following days.

Methodology

Mice: A) A group of five mice was infected with $2 \times 10^5$ plaque forming units (pfu) HSV-1 strain KOS (2) in each eye, and not treated; B) a group of seven mice was infected with $2 \times 10^5$ pfu HSV-1 strain KOS in each eye, and treated with the vehicle only (0.5% ethanol in PBS, no extract); C) a group of six mice was infected with $2 \times 10^5$ pfu HSV-1 strain KOS in each eye, and treated with 2.5 mg/ml of the extract; D) a group of six mice was infected with $2 \times 10^5$ pfu HSV-1 strain KOS in each eye, and treated with 5 mg/ml of the extract; E) a group of seven mice infected with $2 \times 10^5$ pfu HSV-1 strain KOS in each eye, and treated with 10 mg/ml of the extract; and F) a group of two mice was for the mock-infection. The "mock-infection" is a group in which mice receive the same manipulations as other groups except that they do not receive the virus (i.e. only DMEM). This group is a control to verify whether cross-contamination occurred when collecting samples.

All experiments were performed in accordance with the requirements of the institutional committee for the protection of animals. Seven weeks old mice CD-1 from Charles River (St-Constant) and acclimatized for 5 days. The initial infection was performed the same way for each of groups A to E. Mice were anesthetized by injections with ketamine (100 mg/kg)-xylazine (10 mg/kg) diluted in saline. When they no longer had reflexes, their eyes were slightly scarified with a needle. The virus HSV-1 inoculum of $2 \times 10^5$ pfu was diluted in 10 µl DMEM and administered in each eye. Groups B to E were administered the vehicle (Group B) or extract (Groups C to E) at 6, 12, 24, 36, 48 and 60 hours post-infection (hpi). At each of these times, the mice were anesthetized with isoflurane inhalations. The short anesthesia provided sufficient time to deposit 10 µl of the test extract in each eye.

The mice were euthanized by cervical dislocation.

Results

Quantitative evaluation of clinical signs: Mice infected with HSV-1 showed clinical signs that could be quantified with a score from 1 to 4 as follows: 0: no symptom; 1: mild inflammation; 2: mild to moderate inflammation and mild hair loss; 3: moderate to severe inflammation and hair loss with moderate to severe and/or small lesions; and 4: severe inflammation with severe hair loss and severe injuries.

Figure 1:
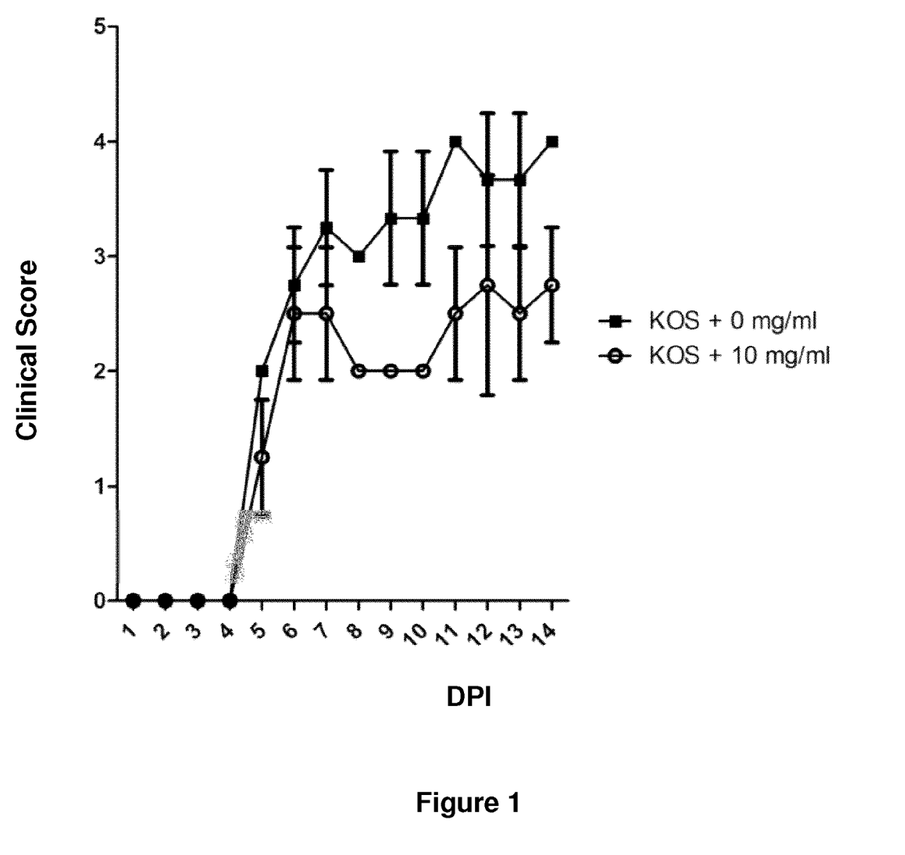
FIG. 1 presents the average clinical score of the disease (y-axis) at different days post-infections (dpi) (x-axis). The results for mice treated with vehicle alone (0 mg/ml) (Group B) and mice treated with 10 mg/ml (Group E) of a *C. canadensis* extract were compared.
Figure 2:
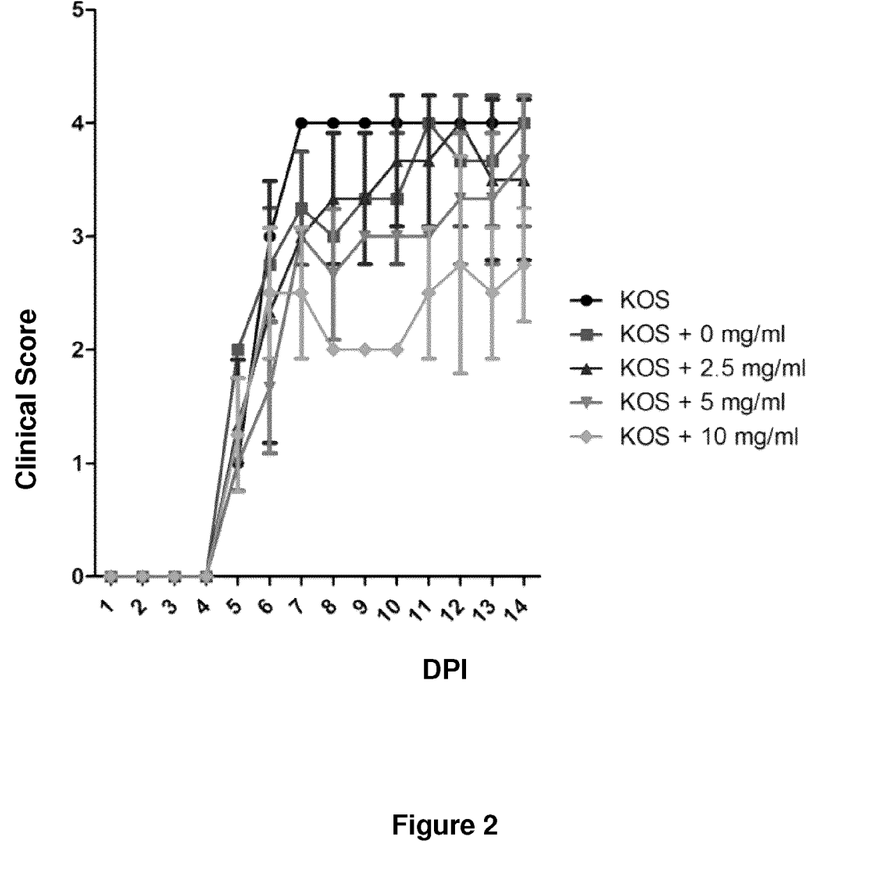
FIG. 2 presents the average clinical score of the disease (y-axis) at different days post-infections (dpi) (x-axis) for all mice groups. KOS: untreated—Group A; KOS+0 mg/ml; treated with vehicle only—Group B; KOS+2.5 mg/ml: treated with 2.5 mg/ml extract—Group C; KOS+5 mg/ml: treated with 5 mg/ml extract—Group D; KOS+10 mg/ml: treated with 10 mg/ml extract—Group E.

Before Day 5 post-infection, the mice did not display any clinical sign. FIG. 1 presents the average clinical score of the disease at different days post-infections (dpi) of mice treated with vehicle alone (0 mg/ml) (Group B) and mice treated with 10 mg/ml (Group E) while FIG. 2 presents the score average with standard deviation for each group of mice assessed on each day. On the 9th, 10th and 11th dpi, the difference between the group treated with 10 mg/ml and the group treated with vehicle alone (Group B KOS+0 mg/ml) was statistically significant according to an ANOVA test and Bonferroni's multiple comparison (*p value <0.05, *** p value <0.001).

Qualitative evaluation of clinical signs Clinical signs of the mice were also qualitatively evaluated in a blind experiment: an individual knowing only that a compound was tested at different concentrations, determined which mice showed the least severe clinical signs. At day 14 post-infection, this individual identified group E (extract at 10 mg/ml), as the group showing the least clinical signs. This is in agreement with the quantitative evaluation.

Certain animals were lost during the experiment. In the majority of these cases, ethical reasons required that mice be sacrificed. A mouse from control Group B (infected and treated with vehicle only—designated KOS+0 mg/ml on FIGS. 1-2) was found dead on the morning of the Day 8 post-infection. A mouse from control Group A (infected, not treated—designated KOS on FIG. 2) had to be euthanized on Day 10 post-infection due to severe weight loss and neurological problems. A mouse from group C (infected and treated with 2.5 mg/ml of extract—designated KOS+2.5 mg/ml on FIG. 2) had to be euthanized on Day 12 post-infection due to neurological problems. However, during the first four days post-infections dpi, the comparison between control group A (infected with virus, not treated), and Groups B to E showed that that the animals tolerated the treatment.

The scope of the claims should not be limited by the preferred embodiments set forth in the examples, but should be given the broadest interpretation consistent with the description as a whole.

REFERENCES

1. Greco, A., Diaz, J. J., Thouvenot, D. and Morfin, F., 2007. Novel targets for the development of anti-herpes compounds. Infectious Disorders Drug Targets 7: 11-18.

2. Koch, C., Reichling, J., Schneele, J. and Schnitzler, P., 2008. Inhibitory effect of essential oils against herpes simplex virus type 2. Phytomedicine 15(1-2): 71-78.
3. O'Brien, J., Wilson, I., Orton, T. and Pognan, F., 2000. Investigation of the Alamar Blue (resazurin) fluorescent dye for the assessment of mammalian cell cytotoxicity. European Journal of Biochemistry 267(17): 5421-5426.
4. Rago, R., Mitchen, J. and Wilding, G., 1990. DNA fluorometric assay in 96-well tissue culture plates using Hoescht 33 258 after cell lysis by freezing in distilled water. Anal. Biochem. 19: 131-34.
5. Russell, W. C., 1962. A sensitive and precise plaque assay for herpes virus. Nature 195(4845): 1028-1029.
6. Smith, J. S. and Robinson, N. J., 2002. Age-specific Prevalence of Infection with Herpes Simplex Virus Types 2 and 1: A Global Review. The Journal of Infectious Diseases 186(S1): S3-S28.
7. Treister, N. S. and Woo, S. B., 2010. Topical n-docosanol for management of recurrent herpes labialis. Expert Opinion on Pharmacotherapy 11: 853-860.
8. Chayavichitsilp P, Buckwalter J V, Krakowski A C, Friedlander S F (April 2009). "Herpes simplex". *Pediatr Rev* 30 (4): 119-29.
9. Coen, D. M., M. Kosz-Vnenchak, J. G. Jacobson, D. A. Leib, C. L. Bogard, P. A. Schaffer, K. L. Tyler, and D. M. Knipe. 1989. Thymidine kinase-negative herpes simplex virus mutants establish latency in mouse trigeminal ganglia but do not reactivate. Proc Natl Acad Sci USA 86:4736-40.
10. Jacobson, J. G., S. H. Chen, W. J. Cook, M. F. Kramer, and D. M. Coen. 1998. Importance of the herpes simplex virus UL24 gene for productive ganglionic infection in mice. Virology 242:161-9.
11. Leib, D. A., C. L. Bogard, M. Kosz-Vnenchak, K. A. Hicks, D. M. Coen, D. M. Knipe, and P. A. Schaffer. 1989. A deletion mutant of the latency-associated transcript of herpes simplex virus type 1 reactivates from the latent state with reduced frequency. J Virol 63:2893-900.
12. Leiva-Torres, G. A., P. A. Rochette, and A. Pearson. 2010. Differential importance of highly conserved residues in UL24 for herpes simplex virus 1 replication in vivo and reactivation. J Gen Virol 91:1109-16.

The invention claimed is:

1. A method of using a plant extract or an active fraction thereof obtained by chromatographic separation of said extract, for inhibiting an herpes simplex virus (HSV) infection or reduce a symptom thereof in a subject in need thereof, the method comprising administering an effective amount of the plant extract or the active fraction thereof to a subject in need thereof, wherein the plant is a (a) *Cornus stolonifera*; (b) *Cornus mas*; or (c) *Cornus Canadensis*.

2. The method of claim 1, wherein the plant is *Cornus stolonifera*.

3. The method of claim 1, wherein the plant extract is an aqueous, alcoholic or hydroalcoholic extract.

4. The method of claim 1, wherein the plant extract is an alcoholic extract that is an ethanolic extract.

5. The method of claim 1, wherein the plant extract is an hydroalcoholic extract that is an hydroethanolic extract.

6. The method of claim 1, wherein the extract is an infusion or a decoction.

7. The method of claim 1, wherein the extract is obtained by reflux.

8. The method of claim 1, wherein the plant extract or active fraction thereof is a flower extract or active fraction thereof, a leaf extract or active fraction thereof or a stem extract or active fraction thereof.

9. The method of claim 1, wherein the HSV is HSV-1.

10. The method of claim 1, further comprising using another agent for inhibiting the herpes simplex virus (HSV) infection.

11. The method of claim 3, wherein the plant extract or active fraction thereof is a flower extract or active fraction thereof, a leaf extract or active fraction thereof or a stem extract or active fraction thereof.

12. The method of claim 4, wherein the plant extract or active fraction thereof is a flower extract or active fraction thereof, a leaf extract or active fraction thereof or a stem extract or active fraction thereof.

13. The method of claim 5, wherein the plant extract or active fraction thereof is a flower extract or active fraction thereof, a leaf extract or active fraction thereof or a stem extract or active fraction thereof.

14. The method of claim 6, wherein the plant extract or active fraction thereof is a flower extract or active fraction thereof, a leaf extract or active fraction thereof or a stem extract or active fraction thereof.

15. The method of claim 9, wherein the plant extract or active fraction thereof is a flower extract or active fraction thereof, a leaf extract or active fraction thereof or a stem extract or active fraction thereof.

16. The method of claim 1, wherein the plant is *Cornus mas*.

17. The method of claim 1, wherein the plant is *Cornus Canadensis*.

18. The method of claim 8, wherein the plant is *Cornus stolonifera*.

19. The method of claim 8, wherein the plant is *Cornus mas*.

20. The method of claim 8, wherein the plant is *Cornus Canadensis*.

21. The method of claim 1, wherein the symptom selected from the group consisting of lesion and inflammation.

22. The method of claim 1, wherein the subject is a human.

* * * * *